United States Patent [19]
Burden et al.

[11] Patent Number: 5,212,362
[45] Date of Patent: May 18, 1993

[54] METHOD AND APPARATUS FOR DISPOSING OF CONTAMINATED HYPODERMIC NEEDLES

[75] Inventors: Roy B. Burden; Michael S. Burden, both of North Bend, Oreg.

[73] Assignee: Sharp-Saf Corporation, North Bend, Oreg.

[21] Appl. No.: 708,398

[22] Filed: May 31, 1991

[51] Int. Cl.⁵ .............................................. B23K 9/013
[52] U.S. Cl. ..................................... 219/69.1; 83/944; 128/919; 219/68
[58] Field of Search ...................... 219/68, 69.1, 69.17; 83/944; 128/919

[56] References Cited
U.S. PATENT DOCUMENTS

| | | | |
|---|---|---|---|
| 4,628,169 | 12/1986 | Ching-Lung | 219/68 |
| 4,877,934 | 10/1989 | Spinello | 219/68 |
| 4,961,541 | 10/1990 | Hashimoto | 219/68 |
| 4,965,426 | 10/1990 | Colombo | 219/68 |
| 5,091,621 | 2/1992 | Butler | 219/68 |

FOREIGN PATENT DOCUMENTS 1-223964 9/1989 Japan ................. 219/69.11

Primary Examiner—Geoffrey S. Evans
Attorney, Agent, or Firm—Klarquist, Sparkman, Campbell, Leigh & Whinston

[57] ABSTRACT

A portable electrical apparatus for destroying contaminated sharp medical instruments. The sharp portion of an instrument is inserted into the apparatus and electrically grounded. An electrically activated electrode is pivotally advanced to approach or contact the point of the sharp instrument to create an electrical arc that progressively volatilizes the sharp portion. A wiper bar dislodges slag from the electrode surface into a receptacle. The contaminated medical instrument is made safe for disposal by the destruction of the sharp portion and by the killing of germs by the heat of the electrical arc.

28 Claims, 4 Drawing Sheets

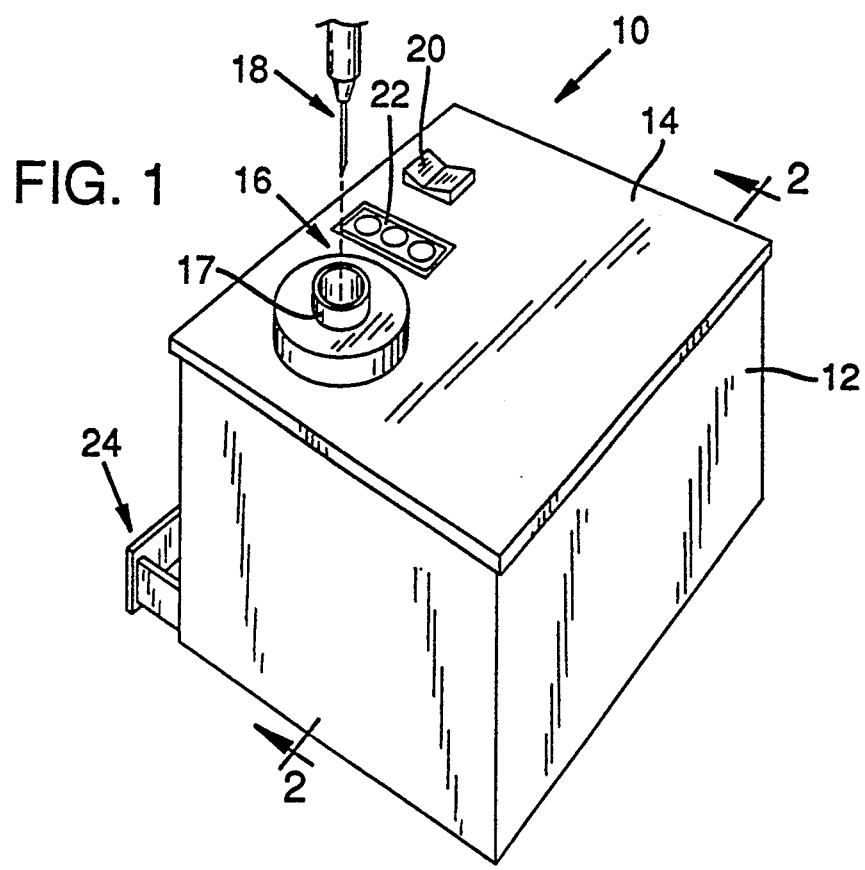
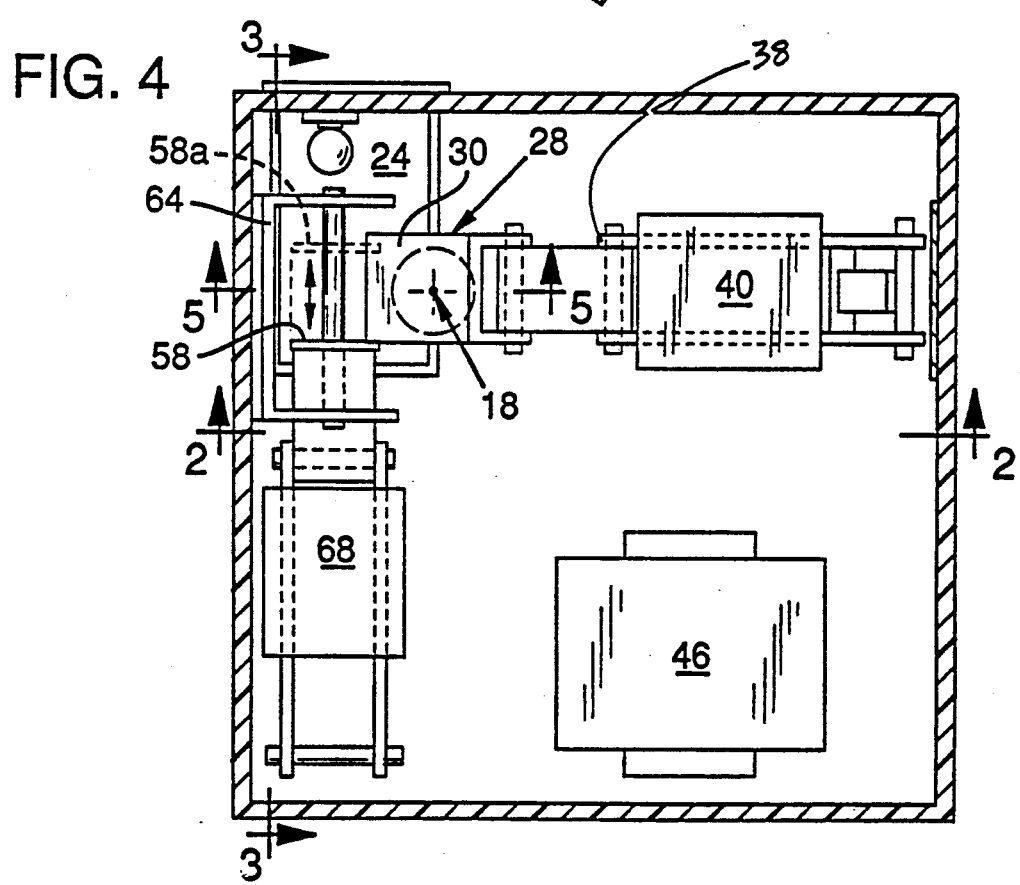

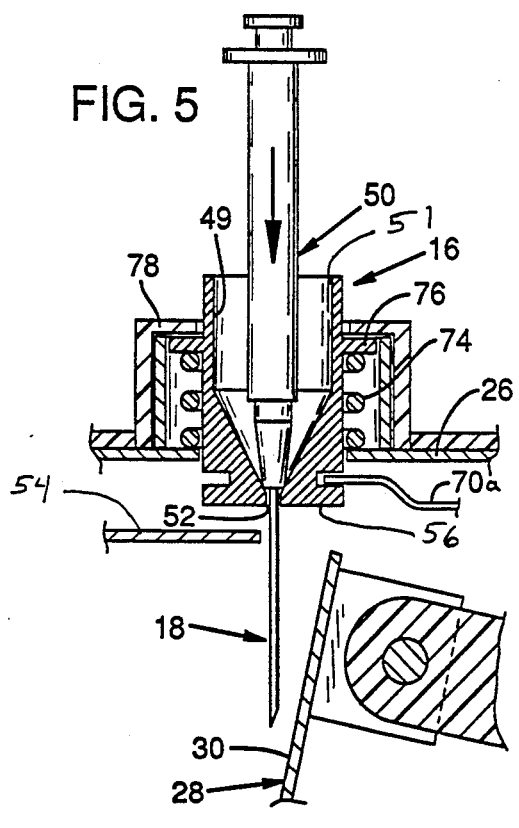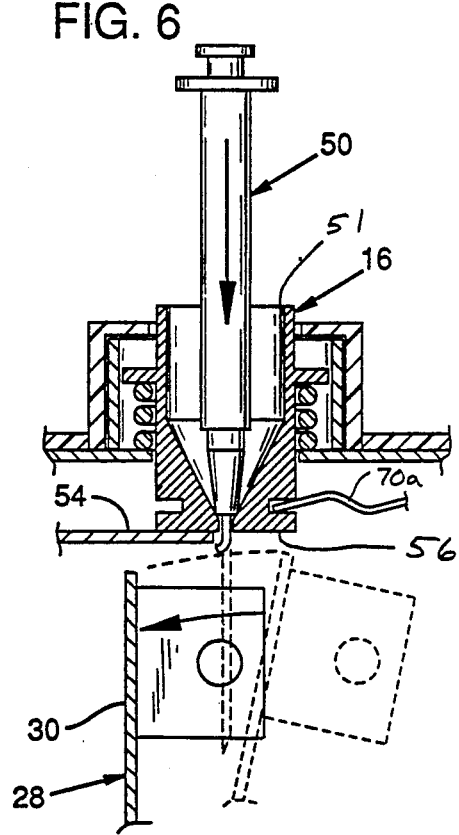

METHOD AND APPARATUS FOR DISPOSING OF CONTAMINATED HYPODERMIC NEEDLES

TECHNICAL FIELD

This invention relates to a method and apparatus for destroying and disposing of contaminated and biohazardous medical sharp instruments such as hypodermic needles.

BACKGROUND OF THE ART

Medical and waste disposal personnel are currently exposed to a risk of injury, infection, disease, and death due to contaminated medical instruments known as "sharps". A hypodermic needle used on an AIDS infected patient, for instance, can transmit the deadly disease to anyone who receives even a minor puncture wound from the hypodermic. Such cases are well documented and can occur any time after the sharp is used, including while the sharp is stored in a clinical setting, during transportation to a waste site, during processing of waste, and after the waste is buried. Hypodermic needles are known to have been disinterred from landfills and to have washed up on beaches. As long as a needle remains sharp, there is a risk of injury and infection.

Used sharps are currently deposited in thick-walled plastic containers immediately after use. These containers are then shipped to waste processing sites where they are typically incinerated. However, the containers remain susceptible to puncture. Also, the contaminated sharps in a container in use may injure and infect medical personnel attempting subsequently to insert a sharp into the container.

There are health hazards associated with the incineration of sharps as well, due to the toxic byproducts of the incineration. In addition, there is always the risk at any time before incineration that a sharp may escape the medical waste disposal system and expose others to health risks.

SUMMARY OF THE INVENTION

The primary object of the invention is to provide a means and method for eliminating the health risks posed during the storage, transportation, and processing of contaminated sharp medical instruments.

According to the present invention, the primary object is achieved by providing a method and means for destroying at least the biohazardous portion of the instrument at its point of use, immediately after its use.

The invention may include a compact, portable unit for destroying the sharp portion of a medical instrument at the site where the instrument is used.

The invention may further include means for electrically volatilizing the sharp portion of the instrument.

The foregoing and additional features and advantages of the present invention will be more readily apparent from the following detailed description which proceeds with reference to the accompanying drawings.

BRIEF DESCRIPTION OF DRAWINGS

FIG. 1 is a perspective view of an apparatus according to the present invention.

FIG. 4 is a sectional view of the apparatus of taken along line 4—4 of FIG. 3.

FIG. 5 is an enlarged sectional view of the apparatus of FIG. 1 taken along line 2—2 of FIG. 1.

FIG. 6 is an enlarged sectional view of the apparatus of FIG. 1 taken along line 2—2 of FIG. 1.

DETAILED DESCRIPTION OF A PREFERRED EMBODIMENT

Figure 2:
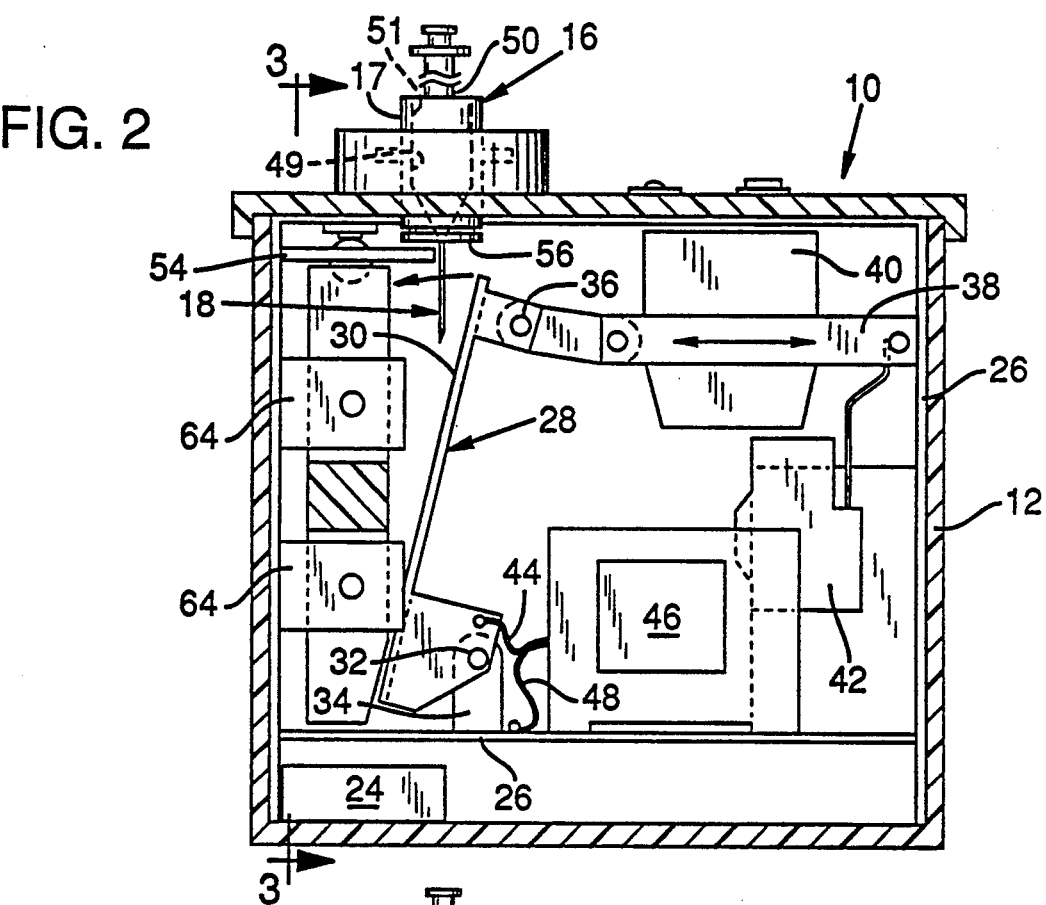
FIG. 2 is a sectional view of the apparatus of FIG. 1 taken along line 2—2 of FIG. 1.

FIG. 1 shows a hypodermic needle volatilizing apparatus 10 constructed in accordance with the invention. A box-shaped enclosure 12 has a cover 14 forming a flat horizontal surface. A hollow cylindrical actuator 16 having an upstanding cylindrical collar 17 is mounted to the cover 14 so that a used hypodermic needle 18 may be inserted vertically downwardly into the actuator 16. A fused illuminated power switch 20 and status indicator lights 22 are also attached to the cover 14. A slag receptacle 24 functions as a drawer that slides in and out of a lower portion of the enclosure 12 generally vertically below the actuator 16.

As shown in FIG. 2, the interior of enclosure 12 is provided on substantially all sides with a ground shield surface 26.

A rigid elongated electrode 28 having a flat rectangular contact surface 30 is pivotally attached at a lower pivot point 32 to an electrically insulating electrode anchor 34 fixed to the enclosure 12 so that the electrode is electrically isolated from the enclosure. The electrode is pivotally attached at an upper pivot point 36 to a slider bar 38 of an electrode solenoid 40 that is fixed to the enclosure 12 by suitable means (not shown). The solenoid 40 is energizable to translate the slider bar 38 from a first position, in which the electrode is oriented at an angle from the vertical (as shown in FIGS. 2 and 5), to a second position in which the contact surface 30 of the electrode 28 is in a more nearly vertical orientation (FIG. 6). An electrode limit switch 42 is fixed to the enclosure 12 and positioned in the path of the slider bar 38 to be actuated thereby when the slider bar has reached the second position and the contact surface 30 of the electrode 28 has reached its more upright orientation.

The electrode 28 is electrically connected to the power output lead 44 of a transformer 46 suitable for converting household AC current to a 12 volt DC output. A ground lead 48 is electrically connected to the ground shield 26.

As best shown in FIGS. 5 and 6 and as further shown in FIG. 2, the actuator 16 is positioned generally vertically above the contact surface 30 of the electrode 28. The cylindrical collar 17 of the actuator 16 defines a tapered bore 49 (shown in FIG. 5) having an upper opening 51 sufficient to permit passage of at least a part of a syringe body 50. The bore tapers to a needle aperture 52 defined in a lower surface 56 of the actuator 16 and sized to permit close passage of the needle 18 therethrough so that the needle will make electrical contact with the actuator 16 at the aperture 52 when the needle is pressed downwardly into the actuator. A horizontal grounding bar 54 is attached to the ground shield 26 of the enclosure 12 so that it extends beneath a portion of the actuator 16. The actuator is constrained to slide axially vertically up and down from a rest position (shown in FIGS. 2 and 5), to an actuated position (shown in FIG. 6) in which the lower surface 56 of the actuator makes electrical contact with the grounding bar 54.

Figure 3:
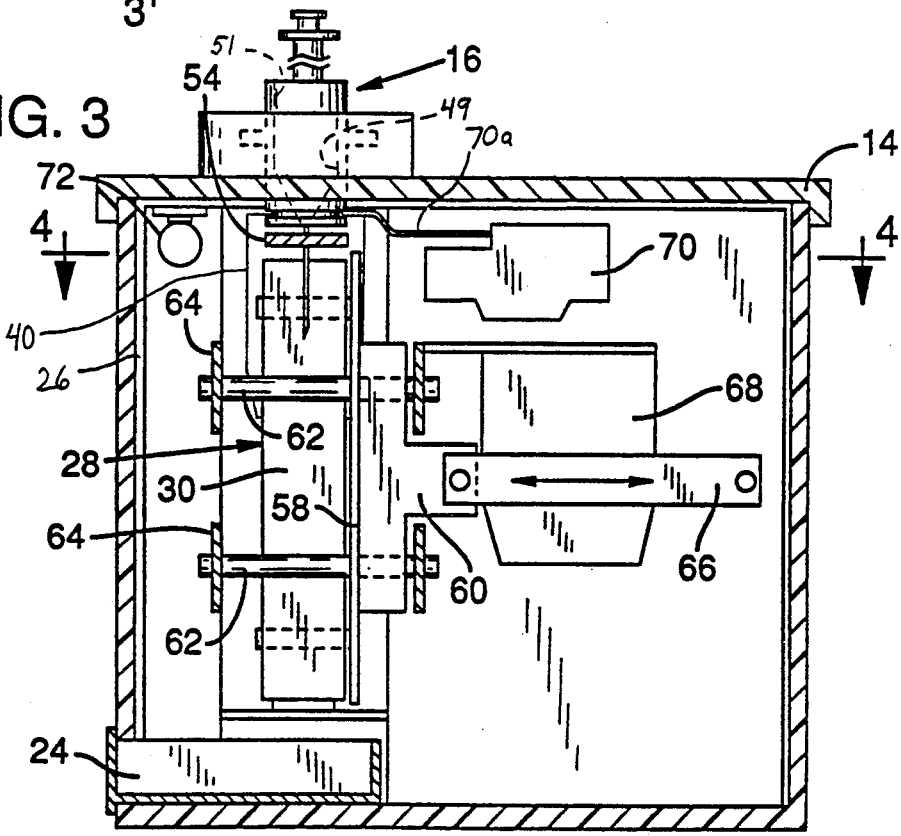
FIG. 3 is a sectional view of the apparatus of FIG. 1 taken along line 3—3 of FIG. 2.

As shown in FIG. 3, an elongated flat rectangular wiper plate 58 is fixed to a wiper pusher block 60 formed of electrically insulating material. The plate 58 and pusher 60 together are mounted on a pair of parallel guide rods 62 mounted to the enclosure 12 by a corresponding pair of U-shaped brackets 64 (see also FIG. 4) so that the guide rods define a horizontal path of the wiper plate 58 across the contact surface 30 of the electrode 28 when the electrode is in its substantially vertical orientation. The wiper pusher 60 is mechanically linked to a wiper slider bar 66 of a wiper solenoid 68 that is fixed to the enclosure. When the solenoid 68 is energized, it will cause the wiper plate 58 to closely pass or scrape over the surface 30 of the electrode 28 from a retracted position (shown in FIG. 3, and in solid lines in FIG. 4) to an advanced position (shown in dashed lines in FIG. 4). The wiper bar thereby dislodges any debris or slag attached to the surface of the electrode so that it falls into the slag receptacle 24. An ultraviolet germicidal lamp 72 is fixed to the cover 14 of the enclosure 12 to kill germs in the debris and to maintain the enclosure in a decontaminated state.

An actuator limit switch 70 is fixed to the housing, connected via switch arm 70a to actuator 16, and arranged to be activated in response to downward motion of the actuator 16 into contact with the grounding bar 54. The limit switch 70 thereby provides a connection to energize the electrode solenoid 40.

In FIG. 4, the limit switches are removed for clarity. The electrode 28 is shown in the initial position (as also illustrated in FIG. 2) with the contact surface 30 aligned directly below the needle 18 (shown here in cross-section). The slider bar 38 of the electrode solenoid 40 is shown in the first position. The wiper bar 58 is shown with the wiper slider bar 66 of the wiper solenoid 68 in the retracted position (in solid lines) and is further illustrated as being moveable into an advanced position 58a (shown in dashed lines).

Operation

The apparatus 10 is normally left in a ready-to-operate mode with the switch 20 remaining in the on position. In this ready state shown in FIG. 1, and illustrated schematically in FIG. 7, the indicator 22 illuminates a green light and electricity is supplied to the UV lamp 72. An operator of the apparatus inserts a sharp instrument, such as the hypodermic needle 18, into the actuator 16 as shown in FIG. 5. An actuator spring 74 provides electrical connection and mechanical compression between the ground shield 26 and an actuator flange 76 that extends about the periphery of the actuator at an intermediate location along its length. The actuator is retained against the spring by an actuator shroud 78 having a flat cylindrical shape with a larger diameter than that of the actuator flange and aligned coaxially with the actuator. The actuator is maintained in electrical connection with the ground shield 26 by the spring 74.

To begin the sequence of needle disposal operations, the operator inserts the syringe 50 into the aperture 16, preferably immediately after the needle is used on a patient near the apparatus. The needle 18 passes substantially through the needle aperture 52. The operator then presses down on the syringe 50 against the biasing force of the spring 74 until the actuator 16 makes contact with the grounding bar 54 as shown in FIG. 6.

Figure 7:
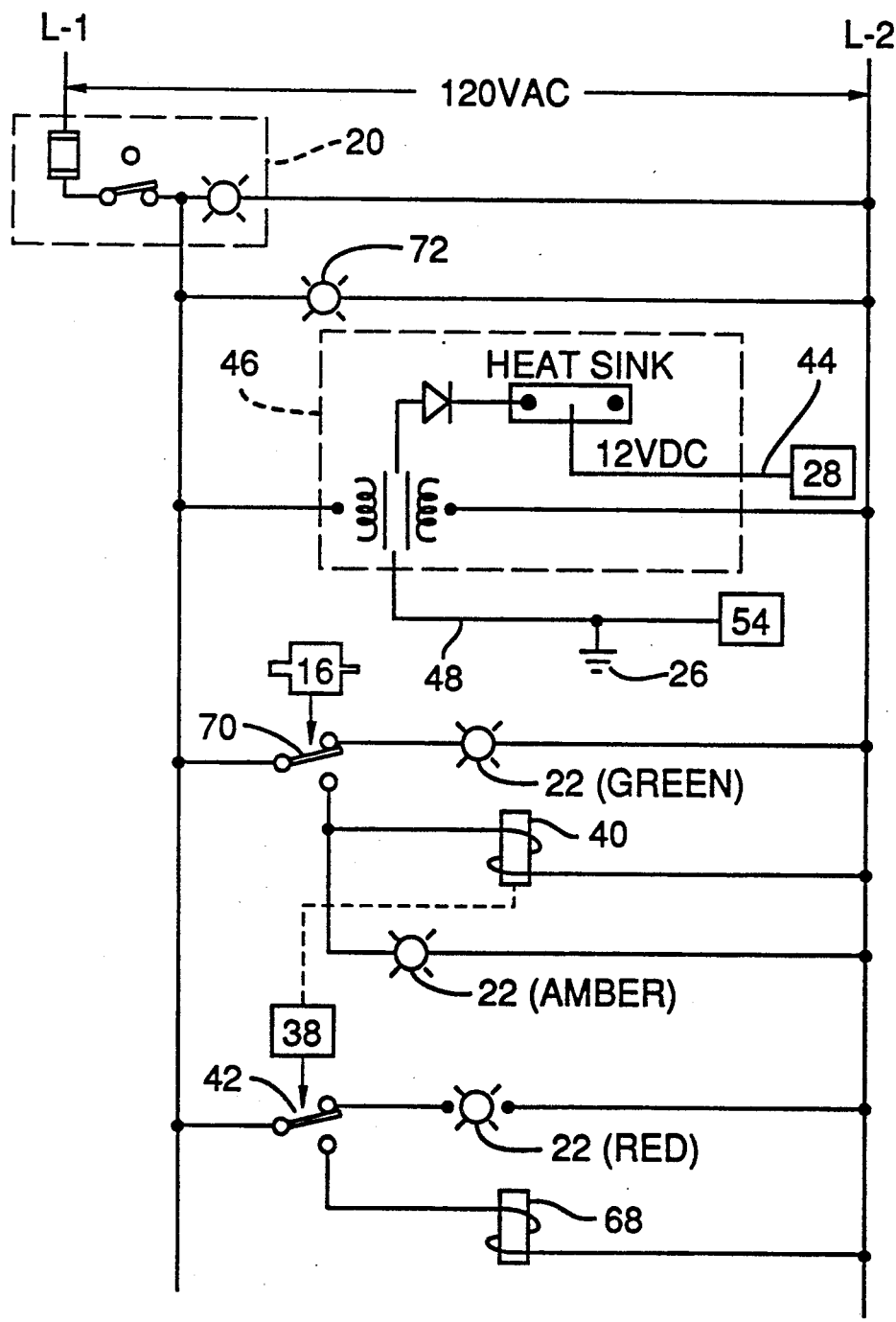
FIG. 7 is an electrical schematic diagram of the apparatus of FIG. 1.

This motion of the actuator deflects the switch arm 70a of the limit switch 70, which provides a connection to energize the electrode solenoid 40, as indicated in FIG. 7.

Consequently, the electrode solenoid 40 shifts the slider bar 38 to cause the electrode 28 to pivot and advance toward the sharp point of the needle 18. Also, the indicator 22 extinguishes the green light and illuminates an amber light to indicate the commencement of the electrode motion. The electrode then makes electrical contact with the point of the needle 18, which is grounded by contact with the needle aperture 52 of the actuator 16. A low voltage electrical arc is thereby formed between the needle and the contacting or nearly contacting electrode surface 30. This electrical arc generates sufficient heat to progressively volatilize the end portion of the needle by melting or vaporizing it.

As the end portion of the needle 18 is volatilized, the electrical arc is maintained between the electrode surface 30 and the remaining portion of the needle 18 by the pivoting motion of the electrode, which advances as the needle erodes. The volatilizing continues until the entire portion of the needle within the path of the electrode is volatilized, permitting the electrode 30 to proceed to its upright position shown in FIG. 6. When the upright position is reached, the electrode limit switch 42 (shown in FIG. 2) provides a connection to energize the wiper solenoid 68 and to illuminate the red light of the indicator 22, as illustrated schematically in FIG. 7.

When the wiper solenoid 68 is energized, the wiper blade 58 advances across the surface of the electrode 28 as shown in FIG. 2, thereby dislodging any slag or melted portions of the needle remaining attached to the electrode surface and depositing such waste in the slag receptacle 24.

As shown in FIG. 7, when the actuator 16 is released, the amber light of the indicator 22 is extinguished, the green light reilluminated, and the actuator limit switch 70 returned to its original state, thereby deenergizing the electrode solenoid 40, which retracts the slider bar 38 and the electrode 28. Consequently, the slider bar 38 releases the electrode limit switch 42, which thereupon disconnects the red light of the indicator 22 and deenergizes the wiper solenoid 68 to retract the wiper 58. The apparatus 10 is thus returned to the ready-to-operate mode.

While the apparatus is described as employing a direct current for volatilizing a needle, it is contemplated that an alternating current could be employed as well. Also, while low voltages have proven effective in the preferred embodiment, it is contemplated that a wide range of voltages may be used effectively.

Thus, having illustrated and described the principles of my invention by what is presently a preferred embodiment, it should be apparent to those persons skilled in the art that the illustrated embodiment may be modified without departing from such principles. I claim as my invention, not only the illustrated embodiment, but all such modifications variations and equivalents thereof as come within the true spirit and scope of the following claims.

I claim:

1. An apparatus for disposing of biohazardous sharp metallic instruments having elongated metallic sharp portions such as hypodermic needles, comprising:

grounding means for electrically grounding the instrument;

an electrode for supplying electricity to the instrument across an arc formed at a position of proximity between the electrode and the instrument; and means for moving the electrode to progressively contact the instrument along its length while the instrument is stationary, such that at least a substantial majority of the biohazardous metallic sharp portion of the instrument is volatilized when an electrical current flows between the electrode and the grounding means.

2. The apparatus of claim 1 including moving means operable upon receipt of an instrument in said receiving means for causing relative movement between said instrument, electrode and grounding means to a volatizing position enabling current flow between said electrode and grounding means through said instrument.

3. The apparatus of claim 1 wherein the electrode supplies direct current to the instrument.

4. The apparatus of claim 1 wherein as the electrode and instrument approach point contact with one another an electric arc is generated between the instrument and the electrode during said approach.

5. The apparatus of claim 4 wherein the electrode comprises a generally flat contact surface and the instrument is an elongated body positioned such that the electrode makes point contact with the instrument.

6. The apparatus of claim 1 comprising receptacle means for receiving waste material from the volatilized instrument.

7. The apparatus of claim 1 wherein the apparatus is embodied in a portable unit for positioning at a site where the instruments are used, whereby temporary storage and transportation of the instruments are not required.

8. The apparatus of claim 1 wherein said receiving means comprises an actuator for receiving the sharp portion of the instrument, the actuator being movable between a first inactive position and a second stationary operating position in which the electrode and grounding means are operable to volatilize the sharp portion, the actuator being spring biased to the first position.

9. The apparatus of claim 8 wherein the electrode is movable to an operable position in response to movement of the actuator to the second position.

10. The apparatus of claim 1 wherein the electrode is operable to supply electricity to the instrument at a voltage of at least 12 volts.

11. The apparatus of claim 1 wherein the electrode is operable to pass direct current through the instrument between the electrode and the grounding means.

12. An apparatus for disposing of biohazardous sharp metallic instruments comprising:
grounding means for electrically grounding the instrument;
an electrode for supplying electricity to the instrument;
a wiper movable across the electrode to dislodge waste material therefrom; and
instrument receiving means operable to position said instrument electrically between said electrode and said grounding means,
such that at least a biohazardous portion of the instrument is substantially volatilized when an electrical current flows between the electrode and the grounding means.

13. The apparatus of claim 12 comprising control means for sequentially actuating the electrode, wiping the electrode, and retracting the electrode.

14. A method of destroying a biohazardous instrument having a sharp portion comprising the steps of:
grounding the instrument;
while grounding the instrument applying a voltage to an electrode;
while grounding the instrument and applying the voltage moving the electrode and sharp portion relative to one another such that the electrode and sharp portion approach one another until electrical current flows across the sharp portion to volatilize said portion; and
wiping the electrode and withdrawing the electrode.

15. A method of destroying a sharp medical instrument having a contaminated elongated metallic portion such as a needle, comprising the steps:
inserting the elongated metallic portion of the instrument into an aperture,
holding the instrument stationary in the aperture,
while the instrument is held stationary, moving an electrode in a path to contact the free end of the instrument and to move progressively along the length of the instrument to electrically destroy substantially the entire elongated metallic portion of the instrument.

16. The method of claim 15 wherein the step of destroying the metallic portion includes forming an electrical arc with the instrument.

17. The method of claim 15 wherein the step of inserting the instrument includes moving the instrument in a first direction, and wherein actuating the actuator includes additionally moving the instrument in the first direction.

18. The method of claim 15 wherein the step of destroying the metallic portion includes applying at least 12 volts across the instrument.

19. The method of claim 15 wherein the step of destroying the metallic portion includes passing a direct current through the instrument.

20. An apparatus for disposing of biohazardous sharp metallic instruments having an elongated sharp portion having a needle length comprising:
instrument receiving means operable to position the instrument in a stationary active position;
grounding means for electrically grounding the instrument in the active position; and
an electrode movable into an operable position relative to the instrument in response to presence of the instrument in the active position for passing an electrical current through the instrument between the electrode and the grounding means, the electrode being movable through a sufficiently wide range of motion to progressively contact the sharp portion throughout substantially the entire needle length;
such that at least a biohazardous portion of the instrument is substantially destroyed by heat generated by the electrical current flowing between the electrode and the grounding means, without moving the instrument during its destruction.

21. The apparatus of claim 20 wherein the instrument receiving means is movable between an inactive position and the instrument active position.

22. The apparatus of claim 20 wherein the instrument receiving means defines an aperture sized to closely receive the biohazardous portion of the instrument such that the instrument is laterally restrained when positioned in the aperture.

23. The apparatus of claim 20 wherein the instrument has a free end and the electrode is movable progressively to approach a point of contact with the free end and thereby destroy progressively a portion of the instrument as the electrical current flows through the instrument between the electrode and the grounding means.

24. The apparatus of claim 20 wherein the electrode is pivotable with respect to the stationary instrument.

25. The apparatus of claim 20 including power supply means for providing a voltage of at least 12 volts between the electrode and the grounding means.

26. The apparatus of claim 20 including power supply means for providing a direct current through the instrument between the electrode and the grounding means.

27. The apparatus of claim 20 including power supply means for providing at least 12 volts direct current to produce an arc at a point of proximity between a free end of the instrument and the electrode.

28. An apparatus for destroying contaminated sharp instruments comprising:
- an instrument receiver movable between a first inactive fixed position and a second inactive fixed position by pushing the instrument into the receiver;
- electrical ground means controllable by the receiver in the second position to complete an electrical circuit;
- a movable electrode movable from an inactive starting position through a path of travel toward the instrument to an extended position upon completion of said electrical circuit;
- said path of travel being selected to cause the electrode as it approaches the instrument to approach the free end of the instrument first and then progressively move along the length of the instrument toward said receiver;
- means for connecting said electrode to a source of electrical power such that with electrode connected to said source and moving in said path of travel toward said instrument, an electrical arc is generated between the free end and the electrode to volatilize the free end and thereafter to progressivley volatilize most of the remaining length of the instrument; and
- means for returning the electrode to its starting position upon movement of the electrode to its extended position.

* * * * *